United States Patent
Compel et al.

(10) Patent No.: US 11,291,203 B2
(45) Date of Patent: Apr. 5, 2022

(54) SOLUBLE METALLOGELS INCLUDING ANTIMICROBIAL SILVER METALLOGELS

(71) Applicants: Lawrence Livermore National Security, LLC, Livermore, CA (US); Colorado State University Research Foundation, Fort Collins, CO (US)

(72) Inventors: William Compel, Oakland, CA (US); Keith Morrison, Livermore, CA (US); James Armstrong, Fort Collins, CO (US); Christopher J. Ackerson, Fort Collins, CO (US)

(73) Assignees: Lawrence Livermore National Security, LLC, Livermore, CA (US); Colorado State University Research Foundation, Fort Collins, CO (US)

(*) Notice: Subject to any disclaimer, the term of this patent is extended or adjusted under 35 U.S.C. 154(b) by 0 days.

(21) Appl. No.: 16/706,553

(22) Filed: Dec. 6, 2019

(65) Prior Publication Data
US 2021/0051948 A1 Feb. 25, 2021

Related U.S. Application Data

(60) Provisional application No. 62/889,497, filed on Aug. 20, 2019.

(51) Int. Cl.
| | |
|---|---|
| *A01N 25/04* | (2006.01) |
| *A61L 15/18* | (2006.01) |
| *A61L 15/20* | (2006.01) |
| *A61L 15/44* | (2006.01) |
| *A61L 15/58* | (2006.01) |
| *A61K 9/06* | (2006.01) |
| *A61K 33/38* | (2006.01) |
| *A61K 47/18* | (2017.01) |
| *A61K 47/20* | (2006.01) |
| *A61L 27/04* | (2006.01) |
| *A61L 27/54* | (2006.01) |
| *C02F 1/50* | (2006.01) |
| *A01N 59/16* | (2006.01) |

(52) U.S. Cl.
CPC ............ *A01N 25/04* (2013.01); *A01N 59/16* (2013.01); *A61K 9/06* (2013.01); *A61K 33/38* (2013.01); *A61K 47/18* (2013.01); *A61K 47/20* (2013.01); *A61L 15/18* (2013.01); *A61L 15/20* (2013.01); *A61L 15/44* (2013.01); *A61L 15/58* (2013.01); *A61L 27/047* (2013.01); *A61L 27/54* (2013.01); *C02F 1/505* (2013.01); *A61L 2300/102* (2013.01); *A61L 2300/104* (2013.01); *A61L 2300/404* (2013.01); *C02F 2303/04* (2013.01)

(58) Field of Classification Search
CPC .. A61K 31/795; A61K 9/5115; A61K 9/5169; A61K 33/38; A61K 47/20
See application file for complete search history.

(56) References Cited

U.S. PATENT DOCUMENTS

| | | | |
|---|---|---|---|
| 8,153,156 B2 | 4/2012 | Ravi | |
| 8,304,257 B2 | 11/2012 | Ackerson et al. | |
| 9,683,992 B2 | 6/2017 | Compel et al. | |
| 10,487,181 B2 | 11/2019 | Compel et al. | |
| 2003/0118729 A1 | 6/2003 | Bishop et al. | |
| 2007/0269594 A1 | 11/2007 | Ackerson et al. | |
| 2009/0130157 A1* | 5/2009 | Ylitalo | B32B 27/36 424/405 |
| 2009/0258202 A1 | 10/2009 | Sakaguchi et al. | |
| 2011/0175040 A1 | 7/2011 | Sakaguchi et al. | |
| 2011/0280914 A1 | 11/2011 | Prestwich et al. | |
| 2011/0313059 A1 | 12/2011 | Blosi et al. | |
| 2013/0095320 A1 | 4/2013 | Sano et al. | |
| 2013/0277625 A1 | 10/2013 | Srinivas et al. | |
| 2014/0329267 A1 | 11/2014 | Odriozola et al. | |
| 2015/0037585 A1 | 2/2015 | Compel et al. | |
| 2016/0375034 A1* | 12/2016 | Baker | A61K 31/095 424/489 |
| 2017/0158824 A1* | 6/2017 | Compel | C09J 185/00 |
| 2019/0283137 A1 | 9/2019 | Compel | |
| 2019/0284348 A1 | 9/2019 | Compel | |
| 2020/0087463 A1 | 3/2020 | Compel et al. | |

FOREIGN PATENT DOCUMENTS

| | | |
|---|---|---|
| CN | 102860325 A * | 1/2013 |
| WO | 2010087912 A1 | 8/2010 |

OTHER PUBLICATIONS

CN-102860325-A (Espacenet English Translation, downloaded Dec. 2020) (Year: 2020).*
Compel et al., U.S. Appl. No. 15/368,232, filed Dec. 2, 2016.
Compel, W., U.S. Appl. No. 15/921,360, filed Mar. 14, 2018.
Compel, W., U.S. Appl. No. 16/352,639, filed Mar. 13, 2019.
Ackerson et al., "Rigid, Specific, and Discrete Gold Nanoparticle/Antibody Conjugates," J Am Chem Soc., 128:2635-2640, Feb. 2006.
Ackerson et al., "Site-Specific Biomolecule Labeling with Gold Clusters," Methods Enzymol., 481:195-230, 2010.
Ackerson et al., "Thiolate Ligands for Synthesis of Water-Soluble Gold Clusters," J Am Chem Soc., 127:6550-6551, Apr. 2005.
Che et al., "Homoleptic Copper(I) Arylthiolates as a New Class of p-type Charge Carriers: Structures and Charge Mobility Studies," Chemistry, 14(10):2965-2975, Mar. 2008.

(Continued)

*Primary Examiner* — Mark V Stevens
(74) *Attorney, Agent, or Firm* — Haukaas Fortius PLLC; Michael H. Haukaas

(57) ABSTRACT

A product includes a metallogel material having metal ions dispersed in an assembly having an organic compound. A method includes combining a metal salt, an organic compound precursor, and a glyme for forming a metallogel material having metal ions dispersed in an assembly having an organic compound.

17 Claims, 4 Drawing Sheets

(56) References Cited

OTHER PUBLICATIONS

Chevrier et al., "Rings, Chains and Helices: New Antimicrobial Silver Coordination Compounds With (Iso-)Nicotinic Acid Derivatives," Dalton Trans., 42(1):217-231, Jan. 2013.
Dharmaratne et al., "Nanocluster Size Evolution Studied by Mass Spectrometry in Room Temperature $Au_2s(SR)_{1s}$ Synthesis," J Am Chem Soc., 131(38):13604-13605, Sep. 2009.
International Search Report and Written Opinion of the ISA/US in PCT/US2016/064784, dated Mar. 27, 2017; 9pgs.
Koivisto et al., "Vibrational Perturbations and Ligand-Layer Coupling in a Single Crystal of $Au_{144}(SC_2H_4Ph)_{60}$ Nanocluster," J Phys Chem Lett., 5(2):387-392, Jan. 2014.
Lavenn et al., "A Luminescent Double Helical Gold(i)-Thiophenolate Coordination Polymer Obtained by Hydrothermal Synthesis or by Thermal Solid-State Amorphous-to-Crystalline Isomerization," J Mater Chem C, 3(16):4115-4125, Apr. 2015.
Liu et al., "Silver(i)-Glutathione Biocoordination Polymer Hydrogel: Effective Antibacterial Activity and Improved Cytocompatibility," J Mater Chem., 21(48):19214-19218, Dec. 2011.
Mandai et al., "Extraordinary Aluminum Coordination in a Novel Homometallic Double Complex Salt," Dalton Trans., 44(25):11259-11263, Jul. 2015.
Meng et al., "Controlled Reduction for Size Selective Synthesis of Thiolate-Protected Gold Nanoclusters $Au_n(n = 20, 24, 39, 40)$," Nanoscale Res Lett., 7(1):277, May 2012.
Mishra et al., "Novel Heterometal-Organic Complexes As First Single Source Precursors for Up-Converting NaY(Ln) F4 (Ln = Yb, Er, Tm) Nanomaterials," Dalton Trans., 41(5):1490-1502, Feb. 2012.
Negishi et al., "Glutathione-Protected Gold Clusters Revisited: Bridging the Gap Between Gold(I)-Thiolate Complexes and Thiolate-Protected Gold Nanocrystals," J Am Chem Soc., 127(14):5261-5270, Mar. 2005.
Odriozola et al., "Gold-glutathione Supramolecular Hydrogels," J Mater. Chem., 17:4843-4845, Oct. 2007.

Pei et al., "Interlocked Catenane-Like Structure Predicted in $Au_{24}(SR)_{20}$: Implication to Structural Evolution of Thiolated Gold Clusters from Homoleptic Gold(I) Thiolates to Core-Stacked Nanoparticles," J Am Chem Soc., 134:3015-3024, Jan. 2012.
Pei et al., "Thiolate-Protected $Au_{20}(SR)_{16}$ Cluster: Prolate $Au_8$ Core with New $[Au_3(SR)_4]$ Staple Motif," J Am Chem Soc., 131:13619-13621, Sep. 2009.
Sarkar et al., "Redox-Switchable Copper(I) Metallogel: A Metal-Organic Material for Selective and Naked-Eye Sensing of Picric Acid," ACS Appl. Mater. Interfaces, 6(9):6308-6316, Apr. 2014.
Schulz-Dobrick, et al., Surfactant-Free Synthesis and Functionalization of Gold Nanoparticles, J Am Chem Soc., 127(37):12816-12817, Aug. 2005, (SI).
Shen et al., "Highly Selective Iodide-Responsive Gel-Sol State Transition in Supramolecular Hydrogels," J Mater Chem., 19(34):219-6224, Sep. 2009.
Taynton et al., "Heat- or Water-Driven Malleability in a Highly Recyclable Covalent Network Polymer," Adv Mater., 26(23):3938-3942, Jun. 2014.
Tofanelli et al., "Superatom Electron Configuration Predicts Thermal Stability of $Au_{25}(SR)_{18}$ Nanoclusters," J Am Chem Soc., 134:16937-16940, Sep. 2012.
Tsukuda, "Toward an Atomic-Level Understanding of Size-Specific Properties of Protected and Stabilized Gold Clusters," Bull. Chem. Soc. Jpn., 85(2):151-168, Feb. 2012.
Walter et al., "A Unified View of Ligand-Protected Gold Clusters As Superatom Complexes," PNAS, 105 (27):9157-9162, Jul. 2008.
Wang et al., "Dynamic Nanoparticle Assemblies", Acc Chem Res., 45(11):1916-1926, Mar. 2012.
Wong et al., "Structure—Activity Relationships for Biodistribution, Pharmacokinetics, and Excretion of Atomically Precise Nanoclusters in a Murine Mode," Nanoscale, 5(21):10525-10533, Nov. 2013.
Zeng et al., "Chiral Structure of Thiolate-Protected 28-Gold-Atom Nanocluster Determined by X-ray Crystallography," J Am Chem Soc., 135:10011-10013, Jul. 2013.
Zhu et al., "Thiolate-Protected $Au_{20}$ Clusters with a Large Energy Gap of 2.1 eV," J Am Chem Soc., 131 (21):7220-7221, May 2009.

* cited by examiner

SOLUBLE METALLOGELS INCLUDING ANTIMICROBIAL SILVER METALLOGELS

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to metallogels, and more particularly, this invention relates to soluble metallogels such as silver metallogels for antimicrobial applications.

BACKGROUND

Silver hydrogels represent a relatively novel biomedical application for antimicrobial wound dressing due to the intrinsic antimicrobial behavior of silver. Silver hydrogels utilize silver nanoparticles for antimicrobial activity. While these materials demonstrate an adequate level of antimicrobial activity, the silver nanoparticles of the silver hydrogels exhibit toxicity, especially at relatively high concentrations. Additionally, silver hydrogels do not include any adhesive properties. Silver hydrogels must be coupled with another material which serves as a binding component. New antimicrobial materials are highly desirable due to the rise of antibiotic-resistant pathogens. Therefore, there is a need for antimicrobial materials which are relatively non-toxic and comprise adhesive properties.

SUMMARY

A product, according to one embodiment, includes a metallogel material having metal ions dispersed in an assembly having an organic compound.

A method, according to another embodiment, includes combining a metal salt, an organic compound precursor, and a glyme for forming a metallogel material having metal ions dispersed in an assembly having an organic compound.

Other aspects and advantages of the present invention will become apparent from the following detailed description, which, when taken in conjunction with the drawings, illustrate by way of example the principles of the invention.

DETAILED DESCRIPTION

Figure 1A:
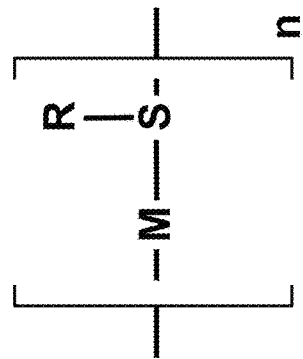
FIG. 1A is a schematic drawing of a metal coordination polymer, according to one embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The following description discloses several preferred embodiments of methods of using metallogels such as silver metallogels for antimicrobial applications.

In one general embodiment, a product includes a metallogel material having metal ions dispersed in an assembly having an organic compound.

In another general embodiment, a method includes combining a metal salt, an organic compound precursor, and a glyme for forming a metallogel material having metal ions dispersed in an assembly having an organic compound.

Silver hydrogels represent a relatively novel biomedical application for antimicrobial wound dressing. Silver hydrogels conventionally utilize silver nanoparticles for antimicrobial activity. Silver nanoparticles exhibit toxicity at high concentrations. Conventional silver hydrogels do not include any adhesive properties and must be coupled with another material which serves as the binding component. Conventional silver hydrogels require a mixture of multiple materials for various applications. Therefore, there is a need for antimicrobial materials which are relatively non-toxic and comprise adhesive properties.

Various embodiments presented herein describe a method of forming and applying metallogel materials of various compositions (e.g., of various metals) in a variety of forms by adjusting a concentration of the metallogel materials in a solvent, e.g., for use as a spray, paste, solution, coating, powder, solid, etc. At least some embodiments described herein disclose silver metallogels which display both antimicrobial and adhesive properties. The silver metallogels comprise silver ions. In stark contrast to conventional silver hydrogels, silver metallogels do not comprise silver nanoparticles, thereby eliminating the toxicity concerns associated with silver hydrogels.

It will be appreciated that the compounds of various embodiments may contain asymmetrically substituted atoms, such as asymmetrically substituted carbon atoms, asymmetrically substituted sulfur atoms, asymmetrically substituted metal atoms, or any combination thereof. All chiral, diastereomeric, racemic forms and all geometric isomeric forms of a structure are part of this disclosure. For example, various reactions may comprise an (R)-cysteine substituent, and (S)-cysteine substituent, or both.

As used herein, a "thiol" refers to an organic compound that includes at least one "—SH" group, which is typically a primary or secondary thiol group, and which can be used as a coinage metal ligand. The thiol can be a water-soluble thiol or organic-soluble thiol. Preferably, the thiol molecule also includes a carboxylic acid or amine moiety.

Examples of suitable water-soluble thiols include, but are not limited to, glutathione, cysteine, captopril, thiomalic acid (mercaptosuccinic acid), N-(2-mercaptopropionyl)glycine, p-mercaptobenzoic acid, m-mercaptobenzoic acid, penicillamine, $(C_2\text{-}C_7)$mercaptoalkanoic acids such as 6-mercaptohexanoic acid, and the like.

Examples of suitable organo-soluble thiols include, but are not limited to, 2-phenylethanethiol (PET), 1-phenylethanethiol, benzyl mercaptan, thiophenol, ($C_1$-$C_{18}$)alkylthiols such as methanethiol, isopropyl thiol, t-butyl thiol, hexanethiol and dodecanethiol, ($C_8$-$C_{18}$)mercaptoalkanoic acids such as 11-mercaptoundecanoic acid, ($C_3$-$C_8$)mercaptocycloalkanes such as cyclohexanethiol, dimercaptosuccinic acid, 2-mercaptoethanol, 3-mercaptopropanol, 3-mercaptopropane-1,2-diol (2,3-dihydroxypropyl-mercaptan; thioglycerol), 1-adamantanethiol, 1-naphthalenethiol, 2-naphthalenethiol, camphorthiol, and the like. Some organo-soluble thiols such as those having a carboxylic acid functionality may become water soluble at high pH (e.g., above about 7, above about 7.5, or above about 8). Organo-soluble thiol derivatives having carboxy or amino functionalities related to the thiols of this paragraph are commercially available or can be prepared synthetically, for use as the thiols of the compositions described herein.

Thiolates typically comprise about 1-30 carbon atoms and may have a wide variety of functional or substituent groups such as oxo (e.g., carbonyl, aldehyde, or ketone) moieties, carboxylic acids, anhydride moieties, ester moieties, amide moieties, cyano, nitro, inorganic acid derivatives (e.g., phospho and boro acids and derivatives) and their sulfur and amino analogs, including I°, II°, III°, and IV° amines, zwitterionic moieties, and various substituents where the substituents may be hydrocarbon or substituted hydrocarbon, as well as carbocyclic and heterocyclic, with functional groups coming within the groups set forth above, as well as nitrogen derivatives, such as azo, azoxy, and diazo, organic and inorganic salts of the above ions, and the like. Complex thiolates may be used, both naturally occurring and synthetic, including oligomers, e.g., oligopeptides, of from about 2 to 30 units, thio analogs of purines, pyrimidines, nucleotides and nucleosides, aptamers, and amide linked nucleic acid analogs.

As used herein, the term "glyme" refers to a glycol ether. One representative example is dimethoxyethane. "Diglyme" refers to diethylene glycol dimethyl ether. Additional glymes include triglyme (triethylene glycol dimethyl ether) and tetraglyme (tetraethylene glycol dimethyl ether).

Glycol ethers can have, for example, a hydroxyl group, an alkyl group, or an ester group as a terminal group, while the other terminal group is typically an alky or phenyl group, but can also be a hydroxyl group. Glymes further include polyethylene glycols of various lengths.

Various embodiments described herein combine organic and inorganic components at a molecular level to allow metals to be processed like plastics. Furthermore, methods using these materials are advantageous in additive manufacturing because the methods enable low-cost and rapid manufacturing of entire functional devices that depend on a metal structure.

Various embodiments described herein include metallogel materials that may be synthesized in various forms, such as, but not limited to a gel, dried to a powder, cast into a mold, deposited as a thin film, extruded into a three dimensional (3D) structure, etc., and may retain unique metallic behavior such as fluorescence, conductivity, catalytic activity, antimicrobial activity, etc.

Various embodiments described herein use methodology disclosed in U.S. patent application Ser. No. 15/368,232 which is herein incorporated by reference. In brief, the methodology describes a process for creating a metallopolymer material (FIG. 1C) that includes metal coordination polymers (FIG. 1A) where M is a metal with physically bound side chains of polymers coordinated with M. The metallopolymer material also includes organic polymers (FIG. 1B) with covalently bound side chains. The metallopolymer material may have the processing capability of polymers while maintaining metallic characteristics.

Persons having ordinary skill in the art would understand upon reading the present disclosure that various embodiments described herein adapt the metallopolymer materials described immediately above for forming metallogel materials comprising metal ions dispersed in an assembly having an organic compound. Specifically, using the approaches disclosed herein, the concentrations of the metallopolymer materials immediately above may be adjusted in a solvent to enable additional applications such as spraying, additive manufacturing, coating, etc.

In one embodiment, the metallopolymer material has a molecular structure that includes a metal-thiolate backbone (-M-S-, FIG. 1C) with covalently bound side chains (solid line, S-R). The covalently bound side chains may provide adaptability for adjustable static properties much like organic polymers, e.g., varying chain length, varying chain flexibility, etc. The physically bound side chains may enable a dynamic bonding environment that renders the material environmentally responsive, e.g., the material possesses correct rheology for shear thinning, define bulk material stiffness, etc. Without wishing to be bound by any theory, it is believed that the physically bound side chains may serve as built-in plasticizer to modulate the structural rigidity of a functional metallopolymer.

Figure 1B:
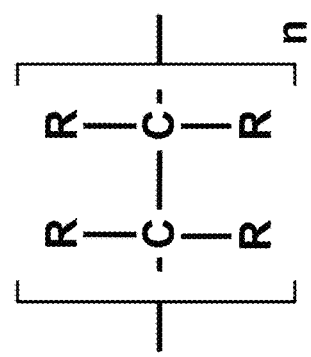
FIG. 1B is a schematic drawing of an organic polymer, according to one embodiment.
Figure 1C:
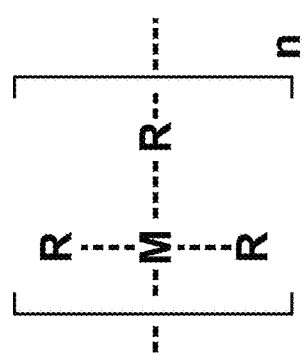
FIG. 1C is a schematic drawing of a metallopolymer material, according to one embodiment.
Figure 1D:
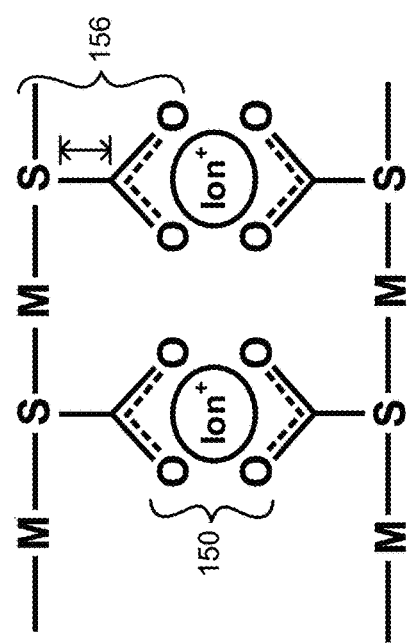
FIG. 1D is a schematic drawing of a proposed mechanism of assembly of a metallopolymer structure, according to one embodiment.

FIG. 1D depicts a schematic representation of a mechanism to create a metallopolymer material 100 that includes ionic bridges 150 and pre-defined polymeric chain length of the thiol ligand 156. According to one embodiment, the metallopolymer segments may perform like plasticizers, as depicted in FIG. 1D, with the thiol ligands 156 providing a site for ionic assembly, as shown with association with the ions (Ion$^+$). Furthermore, the length and flexibility of the covalently bound polymeric chain of the thiol ligand 156 may also affect the ionic conductivity of the ionic bridge 150.

In various embodiments, the ionic conductivity of the metallopolymer material may be tuned based on two factors as shown in FIG. 1D: the strength of the ionic bridge 150 interaction and the flexibility of the polymeric chain of the thiol ligands 156. These two factors may be independently assessed by controlling chemical identity, chain length, and rigidity of the metallopolymer network in silico, i.e., by computer simulation, as discussed further below. In various embodiments described herein, the tunable ionic conductivity of the metallopolymer material may translate into pre-determined tunable ionic conductivity of metal foam formed from the metallopolymer material.

According to one embodiment, the metallopolymer network formed with metallopolymer material may exhibit unique behavior such as ionic conductivity and remarkably high storage modulus that is higher than the sum of the component properties (metal coordination polymers in FIG. 1A and organic polymers in FIG. 1B).

In one approach, metal coordination techniques with organic polymers are synthesized to produce a material with the processing capability of polymers while maintaining metallic character. See FIGS. 1A-1C. Various molecular structures include a metal-thiolate backbone with both covalently and physically bound side chains. The covalently bound side chains provide adaptability for adjustable static properties much like organic polymers. The bulk material exhibits unique behavior such as ionic conductivity and remarkably high storage modulus that cannot be rationalized as a sum of the component properties. Therefore, there is currently no suitable model to evaluate the anomalous behavior of the product based on knowledge of its structure. Structural rigidity emerges as metallopolymer segments assemble through ionic bridges, but ionic conductivity tends to disappear as metallopolymer segments assemble through ionic bridges. See FIG. 1D. Without wishing to be bound by any theory, it is presently believed that the ions become trapped in the assembly.

Figure 2:
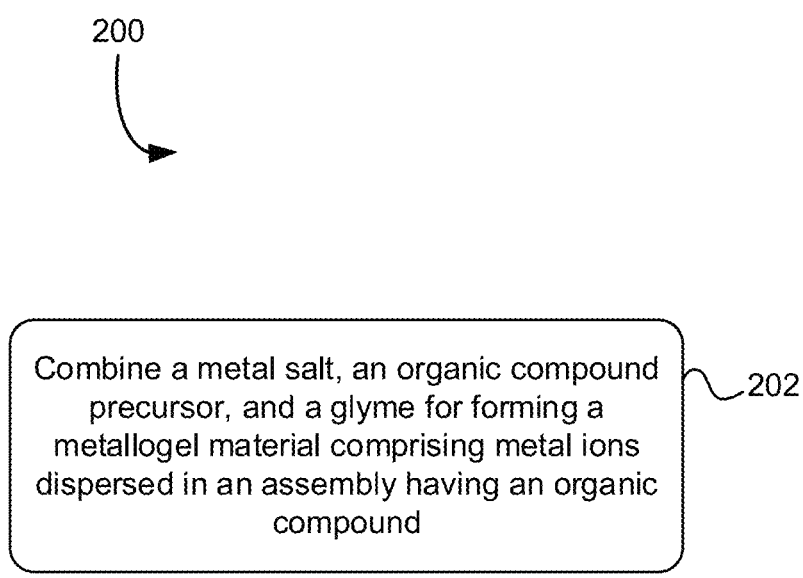
FIG. 2 is a flowchart of a method, according to one embodiment.

Turning now to the figures, FIG. 2 shows a method 200 for forming metallogel materials, in accordance with one embodiment. As an option, the present method 200 may be implemented for forming metallogel materials comprising metal ions such as those shown in the other FIGS. described herein. Of course, however, this method 200 and others presented herein may be used to form metallogel materials for a wide range of purposes and applications which may or may not be related to the illustrative embodiments listed herein. Further, the methods presented herein may be carried out in any desired environment. Moreover, more or less operations than those shown in FIG. 2 may be included in method 200, according to various embodiments. It should also be noted that any of the aforementioned features may be used in any of the embodiments described in accordance with the various methods.

Method 200 includes operation 202 for combining a metal salt, an organic compound precursor, and a glyme for forming a metallogel material comprising metal ions dispersed in an assembly having an organic compound.

In various embodiments of the present invention, metallogel materials are formed by reacting metal salt(s) and an organic compound precursor with a glyme. In preferred embodiments, the metallogel materials comprise metal ions. The metal ions may be gold ions, silver ions, copper ions, zinc ions, or any other metal ion known in the art that is suitable for the intended use of the final product. In a preferred embodiment, the metal ions are silver ions. The metal ions may be derived from metal salts including silver nitrate, copper chloride, gold chloride, etc., or any other metal ion source known in the art.

In various approaches, the organic compound precursor includes a thiol. Any suitable thiol that would become apparent to one skilled in the art upon reading the present disclosure may be used. In preferred embodiments, the organic compound precursor includes cysteine, mercaptosuccinic acid, glutathione, etc. In some approaches, the organic compound precursor may be dissolved in sodium hydroxide prior to and/or during the reaction. For example, cysteine may be dissolved in 0.3 molar sodium hydroxide prior to a reaction with silver nitrate and glyme. In various approaches, the organic compound precursor may be an organic compound which is present in the final product produced according to method 200.

In various approaches, the formation of the metallogel material uses a metal. In a preferred approach, the metal may be a coinage metal. For example, but not intended to be limiting, the coinage metal may be gold (Au), silver (Ag), copper (Cu), etc. In some approaches, the metal may be a combination of metals. For example, but not intended to be limiting, the metal may be a combination of coinage metals. In some approaches, the metal may be tin, platinum, palladium, titanium, aluminum, etc.

In various approaches, the glyme may be defined as a glycol ether, a glycol diether, and any version thereof as described above. In a preferred approach, a volume ratio may be one unit metal ion (e.g., 100 mM silver nitrate) to three units organic compound (e.g., 100 mM cysteine). In preferred embodiments, the glyme is in excess relative to the metal ion. In some approaches, the glyme may be in range of about 100 equivalents to 600 equivalents glyme to one equivalent of metal ion. The concentration of pure glyme, for example mono-, di- tri-, tetra-, pentaglyme, etc., may depend on the molecular weight of the glymes.

In an exemplary approach, a ratio of the thiol to the metal ion at a same concentration may be at least three % vol thiol to one % vol metal ion (e.g., 3:1). In various approaches, the ratio of thiol to metal ion may be a molar ratio of one metal ion to three thiol. Further, a ratio of glyme to a metal ion of a same concentration may be at least 100% vol glyme to 1% vol metal ion (e.g., 100:1). In a preferred approach, the glyme may be in the range of about 100 to about 600 equivalents of polyethylene glycol dimethyl ether (glyme) to one equivalent of metal ion. Further, the molar ratio of the glyme to the metal is at least 6:1. The amount of various glymes, for example mono-, di-tri-, tetra-, pentaglyme, etc. may depend on the molecular weight of the glymes.

In various approaches, the desired metallogel material product precipitates from the reaction and forms a dense, vicious phase at the bottom of the reaction. The precipitated metallogel material exhibits rheological properties that may be dependent on moisture content. In some approaches, the precipitate metallogel material is able to absorb moisture from the surroundings of the material, e.g., the precipitate metallogel material is hygroscopic. The surroundings include the air, atmosphere, etc., surrounding the metallogel material.

Various operations of method 200 include adding a solvent to the metallogel material for changing a physical property of the metallogel material. A physical property of the metallogel material may include a viscosity, a concentration, a physical state (e.g., liquid, gel, paste, spray, solid, powder, etc.), etc. or any other physical characteristic of the metallogel material as would be understood by one having ordinary skill in the art. Using the approaches disclosed herein, the viscosities of the metallogel materials described above may be adjusted to enable additional applications such as spraying, additive manufacturing, coating, etc.

In various embodiments, the metallogel material is a reversible gel. For example, the metallogel material may be dried and reconstituted as a gel as would be understood by one having ordinary skill in the art upon reading the present disclosure. Furthermore, the gel properties are restored after rehydration of the dehydrated gel with the solvent.

In various embodiments of the present disclosure, metallogel materials comprising various metal ions are soluble and/or dissolvable in a solvent. These metallogel materials may be used to form a spray, paste, solution, coating, powder, solid, etc., by adjusting a concentration of the metallogel material in a solvent. Any suitable solvent that would become apparent to one skilled in the art upon reading the present disclosure may be used. In preferred embodiments, the solvent is water.

In a preferred embodiment, metallogel materials are used to form a spray. A spray as used herein refers to the conventional meaning of spray, e.g., a jet of vapor and/or finely divided liquid which is applied as a dynamic collection of drops as would be understood by one having ordinary skill in the art upon reading the present disclosure. In a preferred embodiment, silver metallogels are used to form sprays, pastes, gels, coatings, etc., for antimicrobial applications wherein silver intrinsically exhibits antimicrobial characteristics. In other preferred embodiments, copper metallogels are used to form sprays, pastes, gels, coatings, etc., wherein copper intrinsically exhibits antimicrobial characteristics. Any metal ion metallogel may be used to form sprays, pastes, gels, coatings, etc., as described herein.

Similarly, metallogel materials having other metal ions may likewise be prepared and/or used. Any suitable metal ion may be present. One would expect similar processability and/or characteristics for such metal ions as described herein for silver metallogel materials.

In preferred embodiments, the ratios described herein are based on atomic percentages. In other approaches, the various ratios may be based on percentages of weight, moles, mass, volume, etc.

The metallogel materials described herein may be used to form a spray, paste, solution, coating, powder, solid, etc., by adjusting the ratio of the metallogel material and a solvent. In preferred embodiments, the solvent is water. The ratio may be readily determinable by one having ordinary skill in the art based on known rheology techniques and the intended use of the mixture comprising the metallogel material.

In one embodiment, the mixture comprises about 40 wt % to about 60 wt % water, wherein the mixture is a viscous fluid. In another embodiment, the mixture comprises about 15 wt % to about 40 wt % water, wherein the mixture is a stable gel. In yet another embodiment, the mixture comprises about 0.1 wt % to about 15 wt % water, wherein the mixture is an amorphous solid.

In one approach, the metallogel material is isolated and dried. The metallogel material may be dried to change the viscosity and/or phase of the metallogel in any manner known in the art. The metallogel material may be dried to form a topical gel. For example, the metallogel material may be dried until the viscosity is within a range of about 2 to 10 Pascal-second (Pa·s) (e.g., a range associated with conventional topical treatments as would be understood by one having ordinary skill in the art). In other approaches, the metallogel material may be dried until the metallogel forms a powder. The powdered metallogel material may be stored for future use.

Figure 3:
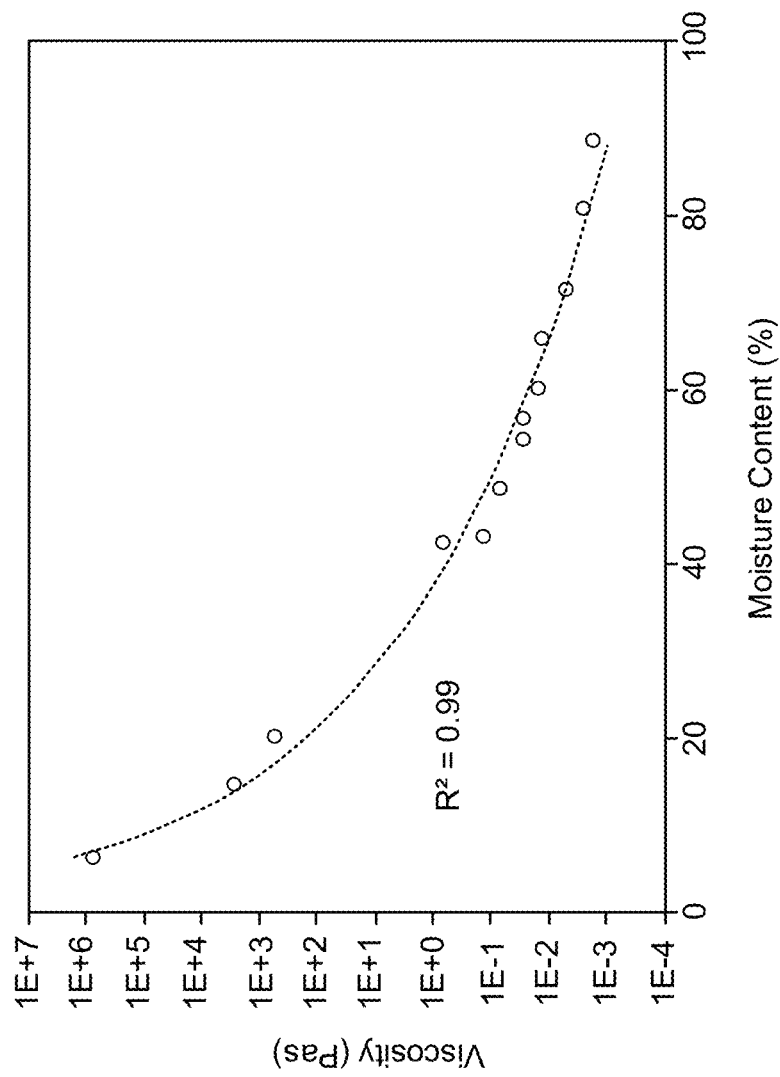
FIG. 3 is a representative chart of viscosity changes of a silver metallogel as a function of moisture content (water content) in weight percent.

FIG. 3 depicts a chart representative of how viscosity changes of a silver metallogel as a function of moisture content (water content) in weight percent.

In one exemplary approach, a powered metallogel material may be reconstituted as a sprayable liquid and/or paste by adjusting the ratio of the metallogel and the solvent (e.g., water) as would be understood by one having ordinary skill in the art.

In an alternative approach, the metallogel material is isolated and diluted to change the viscosity and/or phase of the metallogel material in any manner known in the art. In a preferred approach, the metallogel material may be used to form a sprayable liquid by adjusting the concentration of the metallogel material in a solvent (e.g., water) as would be understood by one having ordinary skill in the art. For example, the metallogel material may be diluted such that the viscosity of the metallogel material in the solvent approaches the viscosity of the solvent (e.g., the theoretical minimum).

In one exemplary embodiment, the viscosity of the metallogel material in the solvent may be in a range of about 0.00169 Pa·s (e.g., approaching the viscosity of water, wherein the water content is about 6.4% by weight (wt %)) to about $7.63288 \times 10^6$ Pa·s (e.g., wherein the water content is about 88.5 wt %).

In preferred approaches, the metallogel material exhibits adhesive properties. The adhesivity of the metallogel material is associated with the amount of solvent the metallogel material is dissolved in in at least some embodiments. In various approaches, the adhesivity of a metallogel material may be readily determinable by one having ordinary skill art based on the techniques described herein and the intended use of the mixture comprising the metallogel material.

In various embodiments, the metallogel material is ionically conductive in amorphous forms. For example, the metallogel material may be ionically conductive as a liquid, gel, paste, spray, etc. Conversely, the metallogel material may not be ionically conductive in solid form because the metal ions are trapped in the assembly (e.g., eliminating the conductivity) as would be understood by one having ordinary skill in the art upon reading the present disclosure.

In Use

In preferred configurations, the metallogel material is uniquely processable. The metallogel materials formed according to embodiments disclosed herein maintain molecular structure as the metallogel material is processed into different physical forms. A metallogel material may form a gel, spray, paste, solution, coating, powder, solid, etc., depending on the amount of solvent used to dilute and/or reconstitute the metallogel material. A viscosity may be readily selectable by one of ordinary skill in the art using known techniques and in consideration of the intended application of the metallogel material.

In various approaches, the metallogel material may be extruded through a nozzle using a Direct Ink Writing (DIW) method of applied manufacturing to print a 3D structure. In other approaches, the metallogel material may be used as an ink in any additive manufacturing technique known in the art. In these approaches, a higher viscosity may be preferred as would be readily determinable by one having ordinary skill in the art using known techniques and in view of the present disclosure. Similarly, metallogel materials having lower viscosities may be used as sprays.

Various metallogel products may be formed according to the above techniques. Potential uses of these metallogel materials includes applications in fields such as agriculture, sensing, adhesives, biomedicine, etc.

In one aspect, the conductive nature of nonsolid metallogel materials may find utility in applications such as electrode adhesives. The metallogel materials as presented herein may be ionically conductive in amorphous forms. It should be understood that, in some embodiments, depending on the disbursement of the metal ions in the metallogel material, portions of the metallogel material may not be ionically conductive. In various approaches, the viscosity (e.g., and a corresponding conductivity) of a metallogel material may be readily determinable by one having ordinary skill art based on the techniques described herein and the intended use of the mixture comprising the metallogel material.

Metallogel materials according to various approaches preferably have adhesive properties, exceptional rigidity, and water solubility. Silver metallogels particularly comprise antimicrobial properties. In one exemplary application, the foregoing properties of silver metallogels may be used in drug-releasing bioscaffolds, wound dressings, topical treatments, etc. In other exemplary applications, copper metallogels may similarly utilize the intrinsic antimicrobial properties of copper for various biomedicine applications. In yet other exemplary applications, zinc metallogels may similarly utilize the intrinsic antimicrobial properties of zinc for various biomedicine applications.

Metallogel materials comprising metal ions with antimicrobial properties are preferred to hydrogels comprising metal nanoparticles. Metal nanoparticles, particularly silver nanoparticles, are toxic in high concentrations. Furthermore, metallic homeostasis processes in bacterium efficiently prevent high levels of metal nanoparticles and/or metal ions from entering the bacteria cells. The metallogel materials disclosed herein are capable of delivering metal ions into bacteria cells in toxic amounts. For example, metallogel materials comprising silver-cysteine structures disguise the metal ions from the bacteria metal-limitation processes. Additionally, the metallogel material structure hinders deactivation of the metal ions which typically occurs in compositions of silver and thiols, for example. The metallogel materials disclosed herein provide a novel delivery route for metal ions which would normally be excluded from cells by homeostasis processes.

Zone of inhibition studies were performed to identify a minimum inhibition concentration for antimicrobial activity of silver metallogels. Cells of a single strain were spread over an agar plate using a sterile swab and incubated in the presence of silver metallogels in varying concentrations. If the bacterial strain is susceptible to the antimicrobial agent, a zone of inhibition appears on the agar plate.

Figure 4:
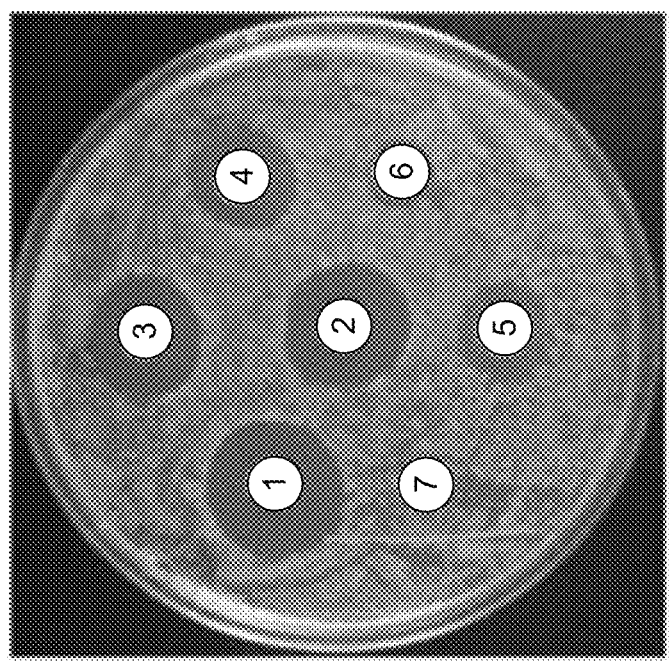
FIG. 4 is an image of an agar plate during a zone of inhibition study of silver metallogels and a table of associated concentrations of the silver metallogels.

FIG. 4 shows seven different concentrations of silver metallogel. A zone of inhibition is presently believed to be as early as 50 µg/mL.

Further disk diffusion testing validated the minimum inhibition concentration between about 25 and about 50 µg/mL. The foregoing range was corroborated by broth and agar dilution testing.

Conventional silver hydrogels exhibit antimicrobial activity between 46 and 53 µg/mL. Silver metallogels therefore show improved antimicrobial activity at lower concentrations of the material compared to conventional silver hydrogels. Silver metallogels may be optimized for even further antimicrobial activity.

The silver ions of the presently disclosed silver metallogels show improved diffusion rates compared to conventional silver hydrogels. Silver ions dispersed in silver metallogels diffuse further than conventional silver ions alone. Metallogels comprising metal ions as disclosed herein may be particularly useful for biofilm applications and/or treating biofilm infections which are relatively difficult to treat due to inaccessibility and/or antibiotic resistivity to certain treatments.

Silver metallogels provide significant improvements upon conventional silver hydrogel techniques. Silver metallogels do not include the use of toxic nanoparticles. Silver metallogels do not require additional adhesive materials to work. Silver metallogels provide a non-toxic, antimicrobial material comprising adhesive properties without any additional components. Silver metallogels may replace current silver nanoparticle hydrogels to become the industry standard for antimicrobial wound dressing and other antimicrobial treatments. Copper and/or zinc metallogels may provide similar improvements over conventional silver hydrogels as would be understood by one having ordinary skill in the art.

In one exemplary application, powdered silver metallogel may be packaged for individual use in a first aid kit. For example, a backpacker may store a package of the powdered silver metallogel in first aid kit and, upon injury, the backpacker may add a small amount of water to form an antimicrobial topical treatment to be applied to the injury and prevent infection. Powdered copper metallogel may be similarly packaged for individual use in a first aid kit.

In the above exemplary application, the powdered metallogel material may be packaged as a kit with associated instructions for adding a solvent (e.g., water) to form an antibiotic paste in case of injury. The powdered metallogel material packaged in a kit form has an extended shelf-life compared to conventional antibiotic ointments which degrade and/or expire relatively quickly.

In other approaches, the metallogel materials may be packaged in a bandage form for providing antibiotic properties to an injury. In some approaches, the metallogel material may be in embedded into the bandage in a powdered and/or solid form. The metallogel material embedded into the bandage may be reconstituted by adding a small amount of solvent (e.g., water) and/or by contact with bodily fluids discharging from the injury. A bandage may include any type of gauze, compression bandage, triangular bandage, tubular bandages, dressing, splint, adhesive dressing, roller bandage, donut bandage, etc.

In one exemplary approach, powdered silver metallogel may be used to purify and/or disinfest various surfaces, substances, etc. For example, powdered silver metallogel may be sprinkled into contaminated water in order to purify the water. Powdered gold metallogel may be similarly sprinkled into a substance and/or onto a surface for purification and/or disinfecting purposes.

The inventive concepts disclosed herein have been presented by way of example to illustrate the myriad features thereof in a plurality of illustrative scenarios, embodiments, and/or implementations. It should be appreciated that the concepts generally disclosed are to be considered as modular, and may be implemented in any combination, permutation, or synthesis thereof. In addition, any modification, alteration, or equivalent of the presently disclosed features, functions, and concepts that would be appreciated by a person having ordinary skill in the art upon reading the instant descriptions should also be considered within the scope of this disclosure.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A method, comprising:
contacting a metallogel material with an object for disinfecting the object and providing adhesion thereto, wherein the metallogel material comprises a coinage metal-thiolate metallopolymer and dispersed silver metal ions having antimicrobial properties, wherein the metallogel material is represented as Formula I:

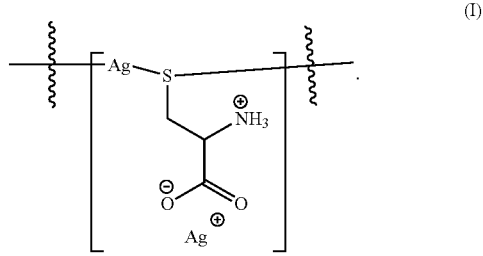

2. The method of claim 1, wherein the contacting includes spraying the metallogel material onto the object.

3. The method of claim 1, comprising altering a viscosity of the metallogel material by adding a solvent thereto prior to the contacting.

4. The method of claim 1, wherein the metallogel material is powdered and packaged in a package, and comprising adding a solvent to the powdered metallogel material for forming an antimicrobial topical treatment, wherein the contacting includes applying the antimicrobial topical treatment to a wound.

5. The method of claim 4, wherein the package is a bandage.

6. The method of claim 1 wherein the dispersed silver metal ions form an ionic bridge between a pair of the coinage metal-thiolate moieties of the metallopolymer.

7. An antimicrobial product, comprising:
a metallogel material comprising a coinage metal-thiolate metallopolymer and dispersed silver metal ions having antimicrobial properties, wherein the metallogel material is represented as Formula I:

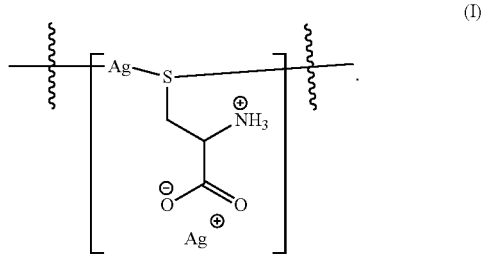

(I)

8. The antimicrobial product of claim 7, comprising a solvent combined with the metallogel material to form an antimicrobial mixture and the antimicrobial mixture is in the form of a spray, paste, or topical gel.

9. The antimicrobial product of claim 7, wherein the dispersed silver metal ions form an ionic bridge between a pair of the coinage metal-thiolate moieties of the metallopolymer.

10. The antimicrobial product of claim 7, wherein the metallogel material has a silver-cysteine structure that is effective to disguise the silver metal ions from bacteria metal-limitation processes.

11. The antimicrobial product of claim 7, wherein the silver metal ions are present in the metallogel material in a concentration of at least 25 µg/mL.

12. A medical product, comprising:
a bandage having coupled thereto the metallogel material according to claim 7.

13. The medical product of claim 12, wherein the metallogel material is coupled to the bandage in a powdered and/or solid form.

14. The medical product of claim 12, wherein the metallogel material coupled to the bandage is configured to function as an adhesive for the bandage.

15. The medical product of claim 14, wherein the metallogel material coupled to the bandage is configured to function as the adhesive for the bandage upon contact of the metallogel material with a solvent and/or a bodily fluid.

16. The medical product of claim 12, wherein the bandage comprises a drug releasing scaffold.

17. The medical product of claim 13 further comprising instructions for adding a solvent to the powdered and/or solid metallogel material to form an antimicrobial topical treatment.

* * * * *